United States Patent
Snyder et al.

(10) Patent No.: US 6,168,926 B1
(45) Date of Patent: Jan. 2, 2001

(54) PROTEIN INHIBITOR OF NEURONAL NITRIC OXIDE SYNTHASE

(75) Inventors: Solomon H. Snyder; Samie R. Jaffrey, both of Baltimore, MD (US)

(73) Assignee: The Johns Hopkins University, Baltimore, MD (US)

( * ) Notice: Under 35 U.S.C. 154(b), the term of this patent shall be extended for 0 days.

(21) Appl. No.: 09/220,574

(22) Filed: Dec. 23, 1998

Related U.S. Application Data

(62) Division of application No. 08/705,625, filed on Aug. 30, 1996, now Pat. No. 5,908,756.

(51) Int. Cl.[7] ............... G01N 33/53; G01N 33/567; C22Q 1/00; C12Q 1/68; C12P 1/00

(52) U.S. Cl. ............... 435/7.1; 435/4; 435/6; 435/7.2; 435/7.21; 435/7.31; 435/7.8; 435/41; 435/69.1; 435/69.7; 435/70.7; 435/70.3; 435/320.1; 530/300; 530/402; 530/827; 530/839

(58) Field of Search ............... 435/7.1, 4, 6, 7.2, 435/7.21, 7.31, 7.8, 41, 69.1, 69.7, 70.1, 70.3; 530/320.1, 300, 402, 827, 839

(56) References Cited

PUBLICATIONS

Rudinger et al. "Peptide Hormones" Edited by Parsons. University Park Press, Jun. 1976.
Burgess et al. J Cell Bio 111:2129–2138, 1990.
Fields et al., "A Novel Genetic System to Detect Protein–Protein Interactions", *Nature* 340:245–246 (1989).
Kavanaugh et al., "An Alternative to SH2 Domains for Binding Tyrosine–Phosphorylated Proteins", *Science* 266:1862–1865 (1994).
Le Douarin et al., "A New Version of the Two–Hybrid Assay for Detection of Protein–Protein Interactions", *Nucleic Acids Research* 23(5):876–878 (1995).
Dick, Thomas et al, "cytoplasmic dynein (ddlc1) mutations cause morphogenetic defects and apoptopic cell death in Drosophila melanogaster" Mol. Cell. Biol., vol. 16, No. 5, May 1996, pp. 1966–1977.
Wilson R. et al., "2.2 Mb of contiguous nucleotide sequence from chromosome III of C. elegans", Nature, vol. 368, 3 Mar. 1994, pp. 32–38.
King S.M. and Patel–King R.S. "The Mr=8,000 and 11,000 outer arm dynein light chains from Chlamydomonas flagella have cytoplasmic homologues" Journal of Biological Chemistry, vol. 270, No. 19, May 12, 1995, pp. 11445–11452.
Jaffrey, Samie R. et al., "Pin: an associated protein inhibitor of neuronal nitric oxide synthase" Science, vol. 274, Nov. 1, 1996, pp. 774–777.

*Primary Examiner*—Phuong T. Bui
*Assistant Examiner*—Li Lee
(74) *Attorney, Agent, or Firm*—Banner & Witcoff, Ltd.

(57) ABSTRACT

An nNOS associated protein designated PIN-1 (Protein Inhibitor of nNOS) has been identified. It physically interacts with nNOS and inhibits its activity. Multiple lines of evidence indicate that PIN-1 is a regulator of nNOS: it is physiologically associated with nNOS, and it inhibits its catalytic activity. The extraordinary evolutionary conservation of PIN-1 and preliminary evidence that it interacts with multiple proteins, suggests that it may be a major biological regulatory protein influencing numerous physiological processes.

4 Claims, 6 Drawing Sheets

MCDRKAVIKN ADMSEEMQQD SVECATQALE
KYNIEKDIAA HIKKEFDKKY NPTWHCIVGR
NFGSYVTHET KHFTYFYLGQ VAILLFKSG

PROTEIN INHIBITOR OF NEURONAL NITRIC OXIDE SYNTHASE

This application is a division of application Ser. No. 08/705,625 filed Aug. 30, 1996, now U.S. Pat. No. 5,908, 756.

The U.S. Government has a paid-up license in this invention and the right in limited circumstances to require the patent owner to license others on reasonable terms as provided for by the terms of USPHS grant DA00266 and Research Scientist Award DA0074 and GM-07309 awarded by the National Institutes of Health.

TECHNICAL AREA OF THE INVENTION

The invention relates to the area of neurotransmitter regulation. More particularly, the invention relates to the regulation of neuronal nitric oxide synthase.

BACKGROUND OF THE INVENTION

Nitric oxide (NO) is a major messenger molecule in the cardiovascular, immune and nervous systems. In the brain, NO is responsible for the glutamate-linked enhancement of 3', 5' cyclic guanosine monophosphate (cGMP) levels (S. R. Jaffrey and S. H. Snyder, *Annu. Rev. Cell Dev. Biol.* 11, 417, 1995) and may be involved in apoptosis (E. Bonofoco et al., *Proc. Natl. Acad Sci. U.S.A.* 92, 7162, 1995; J. B. Mannick et al., *Cell* 79, 1137, 1994), synaptogenesis (Jaffrey and Snyder, ibid.; T. Wang, Z. Xie, and B. Lu, *Nature* 374, 262, 1995) and neuronal development (Jaffrey and Snyder, ibid.).

Since NO cannot be stored in vesicles like other neurotransmitters, its release is regulated by the activity of the enzyme which makes it, NO synthase (NOS). Although a number of substances are known to regulate transcription of NOS, it is possible that regulation occurs at other levels as well. For example, several enzymes are influenced by physiologically associated proteins that serve as enzyme inhibitors. Examples include cyclin-dependent kinase inhibitors (A. Kamb, *Trends Genet.*, 11, 136, 1995; S. J. Elledge and J. W. Harper, *Curr. Opin. Cell Biol.* 6, 847, 1994), the FoF1 ATPase inhibitor (J. E. Walker, *Curr. Opin. Struct. Biol.* 4, 912, 1994), and the ornithine decarboxylase inhibitor antizyme (J. S. Heller, W. F. Fong, E. S. Canellakis, *Proc. Natl. Acad. Sci. U.S.A.* 73, 1858, 1976). Such regulation of NOS by protein inhibitors was not known.

NO mediates glutamate neurotoxicity, which has been implicated in debilitating and lethal neurodegenerative disorders such as Alzheimer's and Huntington's diseases (D. W. Choi, *J. Neurosci* 10, 2493–2501; B. Meldrum and J. Garthwaite, *Trends Phannacol. Sci.* 11, 379–387, 1990). Thus, there is a continuing need in the art of neurotransmitter regulation for methods of affecting the activity of neuronal NOS, so that one can manipulate NO levels when required for therapeutic effect in such disorders.

SUMMARY OF THE INVENTION

It is an object of the invention to provide an isolated mammalian PIN-1 (Protein Inhibitor of nNOS) protein.

It is another object of the invention to provide a fusion protein comprising at least eight contiguous amino acids selected from the PIN-1 amino acid sequence shown in SEQ ID NO:2.

It is yet another object of the invention to provide an isolated polypeptide consisting of at least eight contiguous amino acids of PIN-1 as shown in SEQ ID NO:2 and capable of binding a rat nNOS domain within amino acids 163–245 as shown in SEQ ID NO:3.

It is still another object of the invention to provide a preparation of antibodies which specifically bind to a PIN-1 protein as shown in SEQ ID NO:2.

It is even another object of the invention to provide a subgenomic polynucleotide which encodes a PIN-1 protein as shown in SEQ ID NO:2.

It is yet another object of the invention to provide a recombinant DNA construct for expressing PIN-1 antisense nucleic acids.

It is still another object of the invention to provide a method of inhibiting a mammalian neuronal nitric oxide synthase (nNOS).

It is even another object of the invention to provide methods of screening test compounds for the ability to decrease or augment the activity of nNOS.

These and other objects of the invention are provided by one or more of the embodiments described below. One embodiment of the invention provides an isolated mammalian PIN-1 protein which has the sequence shown in SEQ ID NO:2 and naturally occurring biologically active variants thereof.

Another embodiment of the invention provides a mammalian PIN-1 fusion protein which comprises two protein segments fused to each other by means of a peptide bond, wherein one of the protein segments consists of at least eight contiguous amino acids selected from the amino acid sequence shown in SEQ ID NO:2.

Yet another embodiment of the invention provides an isolated polypeptide which consists of at least eight contiguous amino acids of PIN-1 as shown in SEQ ID NO:2, wherein the polypeptide binds to a rat nNOS domain within amino acids 163–245 as shown in SEQ ID NO:3.

Still another embodiment of the invention provides a preparation of antibodies which specifically bind to a mammalian PIN-1 protein as shown in SEQ ID NO:2.

Even another embodiment of the invention provides a subgenomic polynucleotide which encodes a PIN-1 protein as shown in SEQ ID NO:2.

Yet another embodiment of the invention provides a recombinant DNA construct for expressing PIN-1 antisense nucleic acids, comprising a promoter and a coding sequence for PIN-1 consisting of at least 12 contiguous base pairs selected from SEQ ID NO: 1, wherein the coding sequence is in an inverted orientation with respect to the promoter, such that upon transcription from the promoter an RNA is produced that is complementary to native mRNA encoding PIN-1.

Still another embodiment of the invention provides a method of decreasing a mammalian nNOS, comprising the step of contacting a nNOS with a PIN-1 protein having an amino acid sequence as shown in SEQ ID NO:2.

Even another embodiment of the invention provides a method of screening test compounds for the ability to decrease or augment nNOS activity comprising the steps of: (a) contacting a test compound with a mixture of a mammalian PIN-1 protein and two molecules which bind to each other by virtue of a nNOS dimerization domain or naturally occurring biologically active variants thereof, and (b) measuring the amount of PIN-1 or of at least one of the two molecules that is bound or unbound in the presence of the test compound. A test compound that increases the amount of PIN-1 or decreases the amount of the two molecules that are bound is a potential drug for decreasing nNOS activity. A test compound that decreases the amount of PIN-1 or increases the amount of the two molecules that are bound is a potential drug for augmenting nNOS activity.

In one embodiment of the invention the test compound is contacted with a cell lysate containing nNOS and PIN-1 or naturally occurring biologically active variants thereof. The proteins in the lysate are separated by electrophoresis in an SDS-polyacrylamide gel under non-reducing conditions, and the amount of NNOS monomers or dimers in the gel is measured by immunoblotting. A test compound that decreases the amount of nNOS monomers or increases the amount of nNOS dimers is a potential drug for augmenting nNOS activity. A test compound that increases the amount of nNOS monomers or decreases the amount of nNOS dimers is a potential drug for decreasing nNOS activity.

Yet another embodiment of the invention provides a method of screening test compounds for the ability to decrease or augment nNOS activity comprising the steps of: (a) contacting a cell with a test compound, wherein the cell comprises i) a first fusion protein comprising (1) a DNA binding domain and (2) all or a portion of a mammalian PIN-1 protein, wherein the portion consists of a contiguous sequence of amino acids selected from the amino acid sequence shown in SEQ ID NO:2, wherein the portion is capable of binding to nNOS; ii) a second fusion protein comprising (1) a transcriptional activating domain and 2) all or a portion of nNOS, wherein the portion consists of a contiguous sequence of amino acids selected from amino acids 163–245 as shown in SEQ ID NO:3, or naturally occurring biologically active variants thereof, and wherein the interaction of the portion of the PIN-1 protein with the portion of nNOS reconstitutes a sequence specific transcriptional activating factor; and iii) a reporter gene comprising a DNA sequence to which the DNA binding domain of the first fusion protein specifically binds; and (b) measuring the expression of the reporter gene. A test compound that increases the expression of the reporter gene is a potential drug for decreasing nNOS activity. A test compound that decreases the expression of the reporter gene is a potential drug for augmenting nNOS activity.

Even another embodiment of the invention provides a method of screening test compounds for the ability to decrease or augment nNOS activity comprising the steps of: (a) contacting a cell with a test compound, wherein the cell comprises: i) a first expression vector comprising a subgenomic polynucleotide encoding at least a portion of nNOS or a naturally occurring biologically active variant thereof, wherein the portion of nNOS is capable of binding to at least a portion of PIN-1; ii) a second expression vector comprising a subgenomic polynucleotide encoding at least the portion of PIN-i or a naturally occurring biologically active variant thereof, wherein the portion of PIN-1 is capable of binding to the portion of nNOS; and (b) measuring the amount of cGMP in the cell. A test compound that increases the amount of cGMP is a potential drug for augmenting nNOS activity. A test compound that decreases the amount of cGMP is a potential drug for decreasing nNOS activity.

The present invention thus provides the art with the information that PIN-1, a heretofore unknown protein, regulates the activity of neuronal nitric oxide synthase. PIN-1 can be used, inter alia, in assays to screen for substances which have the ability to decrease or augment neuronal nitric oxide synthase activity.

BRIEF DESCRIPTION OF THE DRAWINGS

FIG. 1. NOS and PIN-1 interact in the yeast two-hybrid system.

FIG. 2. PIN-1 is a highly conserved protein.

FIG. 3. nNOS and PIN-1 interact in vitro.

FIG. 4. PIN-1 inhibits NO generation.

FIG. 5. PIN-1 inhibits NOS dimerization.

DETAILED DESCRIPTION OF THE PREFERRED EMBODIMENTS

Figure 1A:
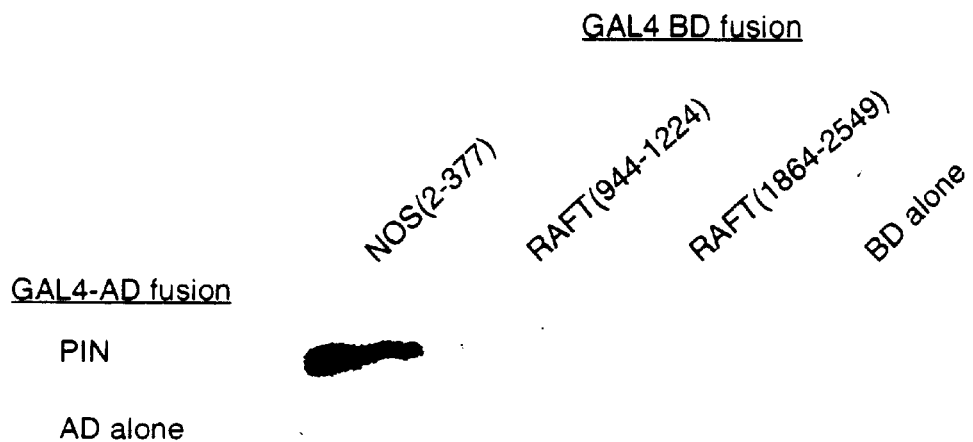
(FIG. 1A) Yeast were transformed with the indicated GAL4 AD and GAL4 BD plasmids and grown on plates containing histidine. A typical filter lift (P. M. Chevray and D. Nathans, PNAS 89, 5789, 1992) is shown in which β-galactosidase activity was detected by the appearance of a dark blue precipitate. pAD-PIN-1 activated LacZ transcription only in the presence of the pBD-NOS (2–377) indicating protein-specific interaction in this system. β-Galactosidase activity correlated with growth on histidine-deficient plates.

It is a discovery of the present invention that the mammalian protein PIN-1 (Protein Inhibitor of nNOS) physically interacts with and inhibits the activity of neuronal nitric oxide synthase (nNOS). Although it was known that nNOS regulates the release of its product, the messenger molecule nitric oxide, protein inhibitors of nNOS were previously unknown.

Mammalian PIN-1 protein has the sequence disclosed in SEQ ID NO:2. Any biologically active variants of this sequence that may occur in mammalian tissues are within the scope of this invention. Biologically active variants bind to and inhibit nNOS. The PIN-1 protein comprises amino acids 1–89 as shown in SEQ ID NO:2. Fragments of a mammalian PIN-1 protein, comprising at least eight, ten, twelve, or fifteen consecutive amino acids selected from the sequence shown in SEQ ID NO:2, may also be used. Such fragments may be useful, for example, in various assays, as immunogens, or in therapeutic compositions. A fusion protein may be used, consisting of a full length mammalian PIN-1 protein or a PIN-1 protein fragment fused to a second protein or protein fragment by means of a peptide bond. The second protein or protein fragment may be, for example, a ligand for yet a third molecule. The second protein or protein fragment may be labeled with a detectable marker or may be an enzyme that will generate a detectable product. A fusion protein may be useful, for example, to target full-length PIN-1 protein or a PIN-1 fragment comprising one or more specific domains, to a specific location in a cell or tissue.

Any of these PIN-1-related proteins may be produced by expressing PIN-1 cDNA sequences in prokaryotic or eukaryotic host cells, using known expression vectors. Synthetic chemistry methods can also be used to synthesize PIN-1 protein, fusion protein, or fragments. Alternatively, PIN-1 protein can be extracted, using standard biochemical methods, from PIN-1-producing mammalian cells, such as brain cells. The source of the cells may be any mammalian tissue that produces PIN-1 protein including human, rat, or mouse. Methods of protein purification, such as size exclusion chromatography, ammonium sulfate fractionation, ion exchange chromatography, affinity chromatography, or preparative gel electrophoresis, are well known in the art. Given the sequence disclosed in SEQ ID NO:2, an ordinary artisan can readily select appropriate methods to obtain a preparation of mammalian PIN-1 protein that is substantially free from other mammalian proteins. An isolated PIN-1 protein is purified from other compounds that may normally associate with PIN-1 protein in a cell, such as certain proteins, carbohydrates, lipids, or subcellular organelles.

The present invention also provides a preparation of antibodies that specifically bind to mammalian PIN-1 protein. The antibodies may be polyclonal or monoclonal and may be raised against biochemically isolated, chemically synthesized, or recombinantly produced full-length PIN-1 protein, PIN-1 protein fragments, or PIN-1 fusion proteins. Techniques for raising antibodies directed against intracellular proteins such as mammalian PIN-1 are well known in the art. The antibodies bind specifically to PIN-1 epitopes, preferably epitopes not present on other mammalian proteins. Antibodies that bind specifically to PIN-1 proteins include those that bind to full-length PIN-1 protein, PIN-1 fragments or degradation products, to alternatively spliced forms of PIN-1 proteins, or to PIN-1 fusion proteins. In preferred embodiments of the invention the antibodies prevent PIN-1 binding to nNOS, immunoprecipitate PIN-1 protein from solution, and react with PIN-1 protein on Western blots of polyacrylamide gels. Preferably the antibodies do not exhibit nonspecific cross-reactivity with other mammalian proteins on Western blots or in immunocytochemical assays. Techniques for purifying PIN-1 antibodies are those which are available in the art. In a more preferred embodiment, antibodies are affinity purified by passing antiserum over a support column to which PIN-1 protein is bound and then eluting the bound antibody, for example with high salt concentrations. Any such techniques may be chosen to achieve the preparation of the invention.

The polynucleotides of the present invention encode PIN-1 protein. These polynucleotides may be isolated and purified free from other nucleotide sequences by standard purification techniques, using restriction enzymes to isolate fragments comprising the PIN-1 encoding sequences. The polynucleotide molecules are preferably intron-free and have the sequence shown in SEQ ID NO: 1. Such PIN-1 cDNA molecules can be made inter alia by using reverse transcriptase with PIN-1 mRNA as a template. The polynucleotide molecules of the invention can also be made using the techniques of synthetic chemistry given the sequence disclosed herein. The degeneracy of the genetic code permits alternate nucleotide sequences to be synthesized that will encode the PIN-1 amino acid sequence shown in SEQ ID NO:2. All such nucleotide sequences are within the scope of the present invention. The PIN-1 polynucleotide molecules can be propagated in vectors and cell lines as is known in the art. The constructs may be on linear or circular molecules. They may be on autonomously replicating molecules or on molecules without replication sequences. Recombinant host cells can be formed by introducing the genetic constructs of the present invention into cells. Any of those techniques which are available in the art can be used to introduce genetic constructs into the cells. These include, but are not limited to, transfection with naked or encapsulated nucleic acids, cellular fusion, protoplast fusion, viral infection, and electroporation. Introduction of genetic constructs may be carried out in vitro or in vivo.

The invention also provides a recombinant DNA construct for expressing PIN-1 antisense nucleic acids. The construct contains a promoter and a coding sequence for PIN-1 consisting of at least 12 and preferably at least 15 or 20 contiguous base pairs selected from SEQ ID NO: 1. The PIN-1 coding sequence is in an inverted orientation with respect to the promoter, so that when the sequence is transcribed from the promoter, an RNA complementary to native PIN-1-encoding mRNA is produced. The construct may also include a terminator at the 3' end of the inverted PIN-1 coding sequence. The antisense molecules produced using the DNA construct of the invention may be used to decrease or prevent the transcription of PIN-1 mRNA. The antisense molecules may be used in vitro or in vivo, as pharmacological agents for the purpose of influencing nNOS activity.

According to the present invention, nNOS is inhibited by mammalian PIN-1 protein, which destabilizes the nNOS dimer, thereby inhibiting nNOS activity. Suitable inhibitory concentrations range from 1 nM to 1 mM. In a preferred embodiment the concentration of PIN-1 protein is at least 250 nM. In a more preferred embodiment the concentration of PIN-1 protein is at least 1 $\mu$M. Greater concentrations of PIN-1 protein may also be used. nNOS activity may be measured, for example, by assaying nitric oxide-dependent cGMP formation in HEK 293 cells cotransfected with DNA encoding PIN-1 and nNOS. Other cell lines, such as mouse N1E-115 neuroblastoma cells, may be used as well. Formation of cGMP may be measured, for example, by radioimmunoassay or by spectrophotometry. nNOS activity may be measured in intact cells or in cell lysates. Other assays for measuring nNOS activity may also be used.

The present invention also provides methods of screening test compounds for the ability to decrease or augment nNOS activity. The test compounds may be pharmacologic agents already known in the art or may be compounds previously unknown to have any pharmacological activity. The compounds may be naturally occurring or designed in the laboratory. They may be isolated from microorganisms, animals, or plants, and may be produced recombinantly, or synthesized by chemical methods known in the art. A test compound can be contacted with a mixture of mammalian PIN-1 protein and two molecules containing, for example, a rat nNOS dimerization domain which is a contiguous sequence selected from the nNOS amino acid sequence shown in SEQ ID NO:3. Analogous domains in other mammalian nNOS proteins can also be used. These are referred to as biologically active, naturally occurring variants of the rat protein. The human nNOS protein is shown as another example of a mammalian nNOS in SEQ ID NO:4. These molecules may be produced recombinantly or may be synthesized using standard chemical methods. One or both of the two dimerizing molecules may consist of less than the entire nNOS momomer. The monomers may be prebound as dimers prior to the step of contacting the test compound. Alternatively, the test compound may contact one of the monomers before the second monomer is added. The dimerization domain-containing molecules may be in solution or one monomer may be bound to a solid support. These molecules may be unlabeled or labeled, for example, with a radioactive, fluorescent, or other detectable marker. They may be fusion proteins comprising a nNOS dimerization domain and another protein with or without a detectable enzymatic activity. The amount of at least one of the two dimerization domain-containing molecules that is bound or unbound in the presence of the test compound is then measured. A number of methods may be used to measure the amount of monomers or dimers. For example, the relative concentration of monomers and dimers may be detected by examining the apparent molecular masses of the molecules by size exclusion chromatography or by polyacrylamide gel electrophoresis under non-reducing conditions. Other methods of measuring binding or dissociation of the dimerization domain-containing molecules will readily occur to those of ordinary skill in the art and can be used. A test compound that decreases the amount of the two molecules that are bound is a potential drug for decreasing nNOS activity. A test compound that increases the amount of the two molecules that are bound is a potential drug for augmenting nNOS activity.

According to another aspect of the invention, a test compound is contacted with a mixture of mammalian PIN-1 protein and molecules containing a nNOS dimerization domain. Binding of the dimerization domain-containing molecules in the presence of the test compound may be measured by detecting dimers or monomers directly or by measuring the displacement of PIN-1 protein. Full-length PIN-1 protein, protein fragments, or fusion proteins may be used. The proteins may be radiolabeled or labeled with fluorescent or enzymatic tags and may be detected, for example, by scintillation counting, fluorometric assay or monitoring the generation of a detectable product, or by measuring their apparent molecular mass by gel filtration or electrophoretic mobility. One of the monomers may be bound to a solid support. A test compound that increases the amount of PIN-1 protein that is bound is a potential drug for decreasing nNOS activity. A test compound that decreases the amount of PIN-1 protein that is bound is a potential drug for augmenting nNOS activity. A test compound which increases dimerization of nNOS is a potential drug for augmenting nNOS activity. A test compound which decreases dimerization of nNOS is a potential drug for decreasing nNOS activity.

According to the present invention a method is also provided of using the yeast two-hybrid technique to screen for test compounds that decrease or augment NNOS activity. The yeast two-hybrid technique is generically taught in Fields, S. and Song, O., Nature 340, 245–46, 1989. In a preferred embodiment, a cell is contacted with a test compound. The cell comprises (i) a first fusion protein comprising a DNA binding domain and all or a portion of a mammalian PIN-1 protein consisting of a contiguous sequence of amino acids selected from the amino acid sequence shown in SEQ ID NO:2 and capable of binding to nNOS; (ii) a second fusion protein comprising a transcriptional activating domain and all or a portion of NNOS, wherein the portion comprises a contiguous sequence of amino acids selected from amino acids 163–245 as shown in SEQ ID NO:3 or naturally occurring biologically active variants thereof, and wherein the interaction of the portion of the PIN-1 protein with the portion of nNOS reconstitutes a sequence specific transcriptional activating factor; and (iii) a reporter gene comprising a DNA sequence to which the DNA binding domain of the first fusion protein specifically binds. When the PIN-1 and nNOS regions are bound together, the DNA binding domain and the transcriptional activating domain will be in close enough proximity to reconstitute a transcriptional activator capable of initiating transcription of a detectable reporter gene in the cell. The expression of the reporter gene in the presence of the test compound is then measured. A test compound that increases the expression of the reporter gene is a potential drug for decreasing nNOS activity. A test compound that decreases the expression of the reporter gene is a potential drug for augmenting nNOS activity. Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16 (See, e.g., G. J. Hannon et al., *Genes Dev.* 7, 2378, 1993; A. S. Zervos et al., *Cell* 72, 223, 1993; A. B. Votjet et al., *Cell* 74, 205, 1993; J. W. Harper et al., *Cell* 75, 805, 1993; B. Le Douarin et al., *Nucl. Acids Res.* 23, 876, 1995). A number of plasmids known in the art can be constructed to contain the coding sequences for the fusion proteins using standard laboratory techniques for manipulating DNA (see, e.g., Example 1, below). Suitable detectable reporter genes include the *E. coli* lacZ gene, whose expression may be measured calorimetrically (see, e.g., Fields and Song, supra), and yeast selectable genes such as HIS3 (Harper et al., supra; Votjet et al., supra; Hannon et al., supra) or URA3 (Le Douarin et al., supra). Methods for transforming cells are also well known in the art. See, e.g., A. Hinnen et al., *Proc. Natl. Acad. Sci. U.S.A.* 75, 1929–1933, 1978. The test compound may comprise part of the cell culture medium or it may be added separately.

In another embodiment, a cell is contacted with a test compound. In this embodiment, the cell comprises (i) a first expression vector comprising a subgenomic polynucleotide encoding at least a portion of nNOS or a naturally occurring biologically active variant thereof, wherein the portion of nNOS is capable of binding to at least a portion of PIN-1, and (ii) a second expression vector comprising a subgenomic polynucleotide encoding the portion of PIN-1 or a naturally occurring biologically active variant thereof, wherein the portion of PIN-1 is capable of binding to the portion of nNOS. The amount of cGMP in the cell is then measured, for example by radioimmunoassay or by spectrophotometry. A test compound that increases the amount of cGMP in the cell is a potential drug for augmenting nNOS activity. A test compound that decreases the amount of cGMP in the cell is a potential drug for decreasing nNOS activity.

The following are provided for exemplification purposes only and are not intended to limit the scope of the invention which has been described in broad terms above.

EXAMPLE 1

This example demonstrates a screen for neuronal nitric oxide synthase associated proteins. This screen was performed using the yeast two-hybrid system (S. Fields and O. -K. Song, *Nature* 340, 245, 1989; P. M. Chevray and D. Nathans, *Proc. Natl. Acad. Sci. U.S.A.* 89, 5789, 1992.)

Yeast expressing a fusion protein consisting of amino acids 2–377 of nNOS and the GAL4 DNA-binding domain (DB) were transformed with a rat hippocampal cDNA library fused to the GAIA activation domain (AD). In this system, protein interaction was detected by growth on histidine-deficient plates and by measuring β-galactosidase activity transcribed off a lacZ reporter gene (P. M. Chevray and D. Nathans, *Proc. Natl. Acad. Sci. U.S.A.* 89, 5789, 1992). Screening ~3×10⁶ clones resulted in the isolation of a complementary DNA (cDNA) that encodes a protein, PIN-1 (Protein Inhibitor of SNOS) that specifically interacts with nNOS. This interaction was specific, as PIN-1 binds to NNOS but not to distinct domains of another protein, the rapamycin and FKBP target (RAFT) (FIG. 1A).

To determine the region of nNOS involved in PIN-1 binding, we expressed several truncated fragments of nNOS as GAL4 DB fusions in yeast and assayed for binding to PIN-1 with the two-hybrid assay. Two-hybrid screens and parent vectors pPC97 and pPC86 were as described in Chevray and Nathans, supra. Plasmid pBD-NOS(2–377) was constructed by inserting a NNOS PCR product comprising amino acids 2–377 into the Sal I-Bgl II sites of pPC97 resulting in an in-frame GAL4 DB-NOS fusion protein. The nNOS fragment was constructed by PCR using the following primers: 5'-GACTAGTCGACTGAAGAGAACACGTTTGGG-3' (coding strand, SEQ ID NO: 5) and 5'-TCTGCAGATCTCAGTGGGCCTTGGAGCCAAA-3' (noncoding strand, SEQ ID NO: 6). A rat hippocampal cDNA library in pPC86 (Li, X. -J. et al., *Nature* 378, 398, 1995) was amplified once in DH1OB (Gibco BRL) (J. Sambrook, E. F. Fritsch, T. Maniatis, *Molecular Cloning: A Laboratory Manual*, Cold Spring Harbor Laboratory Press, Cold Spring Harbor, N.Y., 1989) and transformed into yeast containing pBD-NOS(2–377). pAD-PIN was identified as a 0.5 kb clone which activated LacZ transcription and conferred histidine protrophy in the presence of pBD-NOS (2–377). A double transformant containing pBD-NOS and pPC86 demonstrated that the region of NOS used in the two-hybrid assay was not capable of activating transcription on its own. pPC97 derivatives containing fragments of RAFT were constructed by PCR and cloned into the Sal I and Sac I sites of pPC97. PCRs utilized the following primers: RAFT (1864–2549), 5'-GGACTGGTCGACTGACGAGTTCTACCCCGCC-3' (coding strand, SEQ ID NO: 7) and 5'-GGACTGGAGCTCATCTTGTTGGTC-3' (noncoding strand, SEQ ID NO: 8); RAFT (944–1224)5'-GGACTGGTCGACTCCTCTGCAGAAGAAGGTC-3' (coding strand, SEQ ID NO: 9) and GGACTGGAGCTCTTACCAGAAAGGACACCA-3' (noncoding strand, SEQ ID NO: 10). Truncated NOS fragments comprising amino acids 2–165 and 2–284 were generated by restriction of the initial NOS (2–377) PCR fragment with Nco I and Ava I, respectively followed by Klenow-filling in of that end and ligation into pPC97. Other truncated NOS fragments were prepared by PCR using the following coding strand primers 5'-TAGTCGACTCTCTTCAAACGCAAAGTG-3' (SEQ ID NO: 11) and 5'-TAGTCGACTCAAGGCCATGGGCAGGGA-3' (SEQ ID NO: 12) for creating N-terminal fragments beginning at amino acids 20 and 163, respectively. Truncations ending at amino acid 245 utilized the following noncoding strand primer: 5'-GCAGATCTTTGTGCGATITGCCATC-3' (SEQ ID NO: 13). Sequences of newly constructed plasmids were confirmed by automated fluorescent sequencing.

Figure 1B:
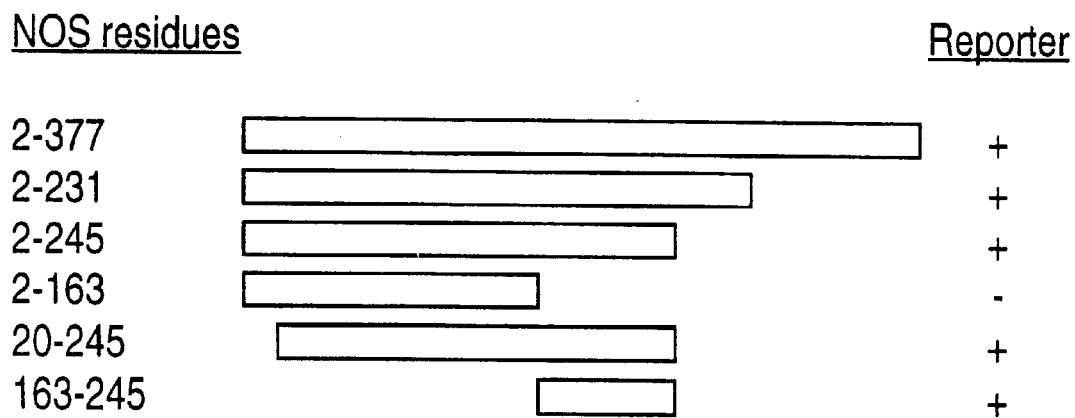
(FIG. 1B) Mapping of the PIN-1-binding domain of nNOS. The GAL4 BD was fused to regions of NOS and the ability of these proteins to interact with PIN-1 was assayed using the yeast two-hybrid assay. The relative β-galactosidase activity is indicated in the column on the right.

A fusion protein containing amino acids 163–245 of nNOS was sufficient for PIN-1 binding (FIG. 1B). This region lies outside of the NOS PDZ domain, a protein-binding module that may target NOS to synaptic or cytoskeletal structures (C. P. Pontig and C. Phillips, *Trends Biochem. Sci.* 20, 102, 1995; J. E. Brenman et al., *Cell* 82, 743, 1995; J. E. Brenman et al., *Cell* 84, 757, 1996), and also does not overlap with regions of NOS previously implicated in binding to calmodulin or cofactors.

EXAMPLE 2

This example demonstrates the tissue distribution of PIN-1 mRNA.

Northern (RNA) blot analysis using the PIN-1 cDNA revealed a 0.9 kb transcript, with highest levels in the testes, various brain regions providing the next highest levels, and most peripheral tissues containing significantly less but detectable levels. In the brain, the transcript was abundant, appearing to be present at levels nearly as high as the glyceraldehyde-3-phosphate dehydrogenase transcript.

EXAMPLE 3

This example demonstrates the determination of the full length PIN-1 coding sequence.

To obtain the full length PIN-1 sequence, a rat brain cDNA library was screened with the PIN-1 cDNA from the yeast two-hybrid system. A pBluescript plasmid containing the cDNA for PIN was obtained by screening a rat brain IZAPII cDNA library (Stratagene) with a randomly primed $^{32}$P-labelled probe derived from the Sal I-Not I insert in pAD-PIN. Library screening was performed according to the directions of the manufacturer. Sequencing of the pAD-PIN insert and the Bluescript clone confirmed that they were identical.

We obtained a 615 bp cDNA which contained a 270 bp open reading frame preceded 87 bases upstream by an in-frame stop codon. The start codon was assigned as the first ATG and was located in a context that conformed to the Kozak consensus sequence (M. Kozak, *J. Biol. Chem.* 266, 19867, 1991). These data revealed that the clone initially obtained in the yeast two-hybrid screen coded the complete PIN-1 sequence and 25 amino acids from the 5' untranslated region.

EXAMPLE 4

This example demonstrates the predicted amino acid sequence and characteristics of mammalian PIN-1 protein.

Figures 2A, 2B:
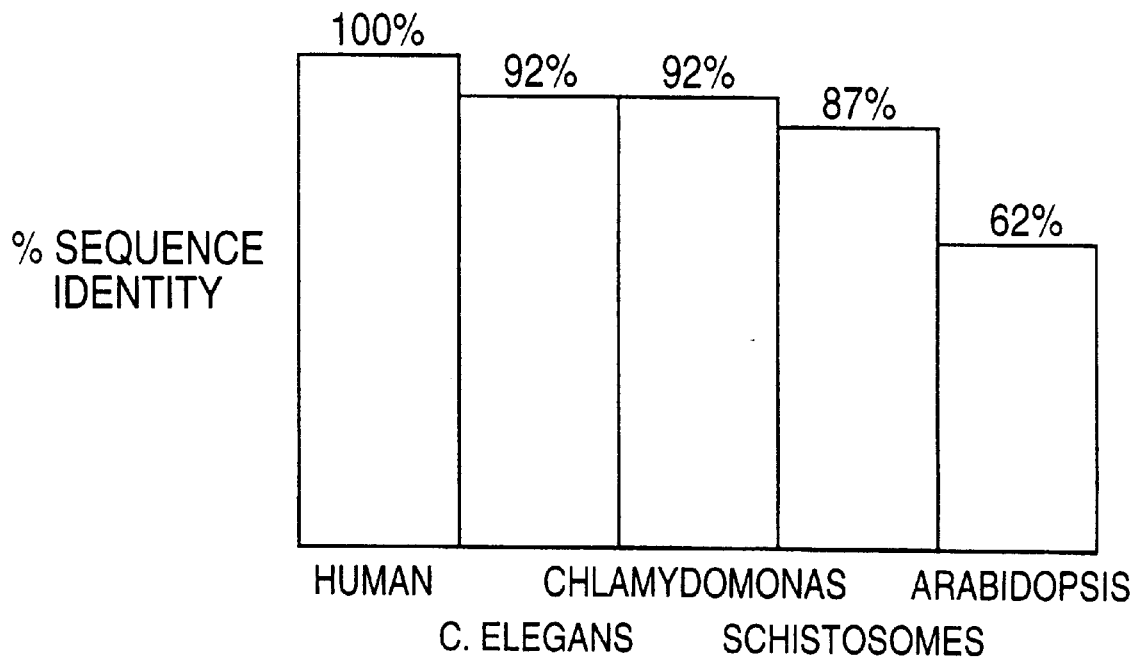
(FIG. 2A) Amino acid sequence of PIN-1. Abbreviations for the amino acids residues are A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.
(FIG. 2B) PIN-1 is highly conserved in different species. Predicted amino acid sequences from ESTs representing PIN-1 homologs were compared to the rat PIN-I sequence and the percent amino acid sequence identity is indicated above each bar. Accession numbers for the referenced clones are:N28047 (EST, *S. mansoni*), T01352 (EST, *C. reinhardtii*), T34147 (EST, human), T88069 (*A. thaliana*).

PIN-1 is predicted to be an 89 amino acid protein (FIG. 2A) and has no recognizable motifs. A database search (S. F. Altschul et al., *J. Mol. Biol.* 215, 403, 1990) reveals that PIN-1 has 92% amino acid sequence identity to a hypothetical protein identified in the C. elegans genome sequencing project (R. Wilson et al., *Nature* 368, 32, 1994) and has 92% amino acid sequence identity to a *Chlamydomonas reinhardtii* protein of unknown function recently identified as a component of a macromolecular complex which includes flagellar dynein (S. M. King and R. S. Patel-King, *J. Biol. Chem.* 270, 11445, 1995). The level of sequence identity implies that PIN-1 is the rat homolog of these proteins. The search also identified expressed sequence tags (ESTs) from several species encoding PIN-1 homologs. These ESTs, some of which span the entire or nearly the entire coding sequence of PIN-1, reveal that PIN-1 is highly conserved across species (FIG. 2B). Thus, rat PIN-1 displays 92% amino acid sequence identity with the *C. elegans* and Chlamydomonas homologs and 100% identity with the human and mouse sequences (FIG. 2B). Accession numbers for the referenced clones are:N28047 (EST, *S. mansoni*), T01352 (EST, *C. reinhardtii*), T34147 (EST, human), T88069 (*A. thaliana*). Sequences were aligned using BLAST (S. F. Altschul et al., *J. Mol. Biol.* 215, 403, 1990), and amino acid identity was determined by dividing the number of identical amino acids by the total number of compared amino acids. Ambiguous nucleotides from the ESTs which could not be translated were omitted from the analysis. Even the Arabidopsis homolog displays 62% identity to rat PIN-1 (FIG. 2B). This remarkable conservation is reminiscent of highly conserved proteins such as FKBP-12 (J. J. Siekierka et al., *J. Biol. Chem.* 265, 21011, 1990), cyclophilin (N. Takahashi et al., *Nature* 337, 473, 1989; G. Fischer et al., *Nature.,* 337, 476, 1989) and the 14-3-3 family (A. Aitken et al., *Trends Biol. Sci.* 17, 498, 1992). Accordingly, it is likely that PIN-1 serves important, conserved biological functions. Preliminary yeast two-hybrid and blot overlay experiments reveal specific associations of PIN-1 with several other proteins besides nNOS. Thus, PIN-1's biological function may involve association with numerous proteins.

EXAMPLE 5

This example demonstrates the interaction of PIN-1 and neuronal nitric oxide synthase.

We confirmed the interaction of PIN-1 and nNOS by several techniques. We examined the ability of nNOS, endothelial NOS (eNOS), and inducible NOS (iNOS) in lysates from transfected human embryonic kidney (HEK) 293 cells to bind to a glutathione-S-transferase (GST)-PIN-1 fusion protein and not to GST. The cDNA for PIN was excised from pAD-PIN with Sal I and Not I and cloned into those sites in pGEX-4T2 (Pharmacia) resulting in an in frame GST fusion protein. Fusion proteins were prepared in *E. coli* BL21(DE3) (Novagen) with glutathione-agarose (Sigma) as described in D. B. Smith and K. S. Johnson, Gene 67, 31, 1988, except that bacterial pellets were lysed in lysis buffer (50 mM tris-HCl, pH 7.7, 100 mM NaCl, and 2 mM EDTA), supernatants were adjusted to 1% Triton X-100, and protein was purified using elution buffer (50 mM tris-HCl, pH 7.7, 100 mM NaCl, 10 mM reduced glutathione, and 2 mM EDTA). HEK 293 cells were transfected with plasmids for nNOS [D. S. Bredt et al., *Nature* 351, 714, 1991), eNOS (S. Lamas et al., *Proc. Natl. Acad. Sci. U.S.A.* 89, 6348, 1992), and iNOS (C. J. Lowenstein et al., *Proc. Natl. Acad. Sci. U.S.A.* 89, 6711, 1992). Transfections were performed with 10 mg of each plasmid using the calcium phosphate method (J. Sambrook, E. F. Fritsch, T. Maniatis, *Molecular Cloning: A Laboratory Manual,* Cold Spring Harbor Laboratory Press, Cold Spring Harbor, N.Y., 1989). Following transfection, cells were sonicated in buffer A (50 mM tris-HCl, pH 7.7, 100 mM NaCl, 2 mM EDTA, and 1% Triton X-100) and cleared by centrifugation. This cellular lysate was incubated with GST or GST-PIN immobilized on glutathione-agarose for one hour at 4° C. and washed extensively in HNTG buffer (20 mM Hepes, pH 7.4, 500 mM NaCl, 10% glycerol, and 0.1% Triton X-100). The material remaining on the resin was eluted with SDS-PAGE sample buffer and nNOS was detected by immunoblot using antibodies specific to each NOS isoform (Transduction Labs).

For assays testing PIN binding to immobilized NOS, 20 mg of bacterial lysate was added to 200 mg of transfected HEK 293 cell lysate and bound to 2', 5', ADP-Sepharose 4B (Pharrnacia) and subsequently washed and eluted with 10 mM NADPH as described in D. S. Bredt et al., *Proc. Natl. Acad. Sci. U.S.A.* 87, 682, 1990. The eluate was immunoblotted with a rabbit polyclonal anti-GST antibody (NovaCastra). For blot-overlay analysis, pGEX-4T2 was modified such that two sites for protein kinase A (PKA) encoded on complementary synthetic oligonucleotides (5'-AATTCGTCGTGCATCTGTTGAACTACGTCGAGC TTCAGTTGCG-3' (SEQ ID NO: 14)and 5'-TCGACGCAACTGAAGCTCGACGTAGTFCAA CAGATGCACGACG-3' (SEQ ID NO: 15)) were ligated into the Eco RI-Sal I sites in the multiple cloning site to generate plasmid pGEX4T-2K. Kinase reactions and blot overlays were performed as described in W. M. Kavanaugh and L. T. Williams, *Science* 266, 1862, 1994. Immunoblots and imunoprecipitation utilized the anti-myc monoclonal antibody 9E10 (Oncogene Science, Cambridge, Mass.).

Figure 3A:
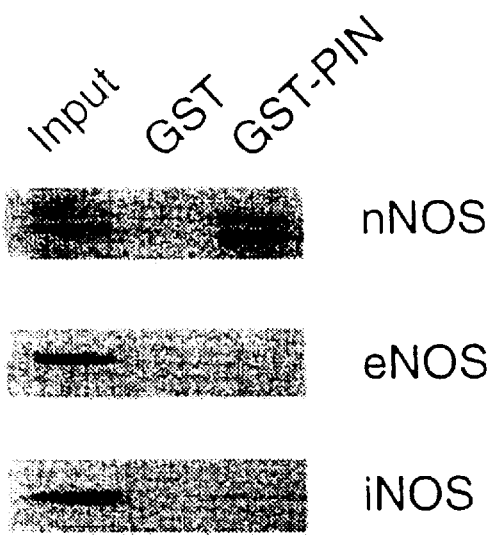
(FIG. 3A) PIN-1 binds to nNOS but not iNOS or eNOS. Bacterially expressed GST-PIN-1 and GST were bound to glutathione agarose. Lysates of HEK 293 cells transfected with expression plasmids for nNOS, iNOS, and eNOS were applied to the GST fusion protein columns and incubated for one hour at 4° C. (20). The contents of the resin were eluted with SDS-PAGE sample buffer and immunoblotted with the indicated isoform-specific antibodies.

Immunoprecipitations were performed as follows. Transfections of HEK 293 cells were performed in 10 cm petri dishes. Cells were scraped and sonicated in 0.5 ml lysis buffer. Supernatants were prepared by centrifugation at 14,000× g for 10 min at 4° C. To 100 ml of supernatant was added 0.5 mg of anfi-myc antibody and 10 ml of protein G-sepharose (Oncogene Science). Following overnight incubation, the resin was washed extensively, the contents were eluted in SDS-PAGE sample buffer and immunoblotted with an anti-nNOS antibody. nNOS specifically associated with PIN-1, but eNOS and iNOS did not (FIG. 3A). The domain of nNOS that binds to PIN-1 resides between amino acids 163 and 245 (FIG. 1B), which are absent in eNOS and iNOS, accounting for their failure to bind to PIN-1.

Figure 3B:
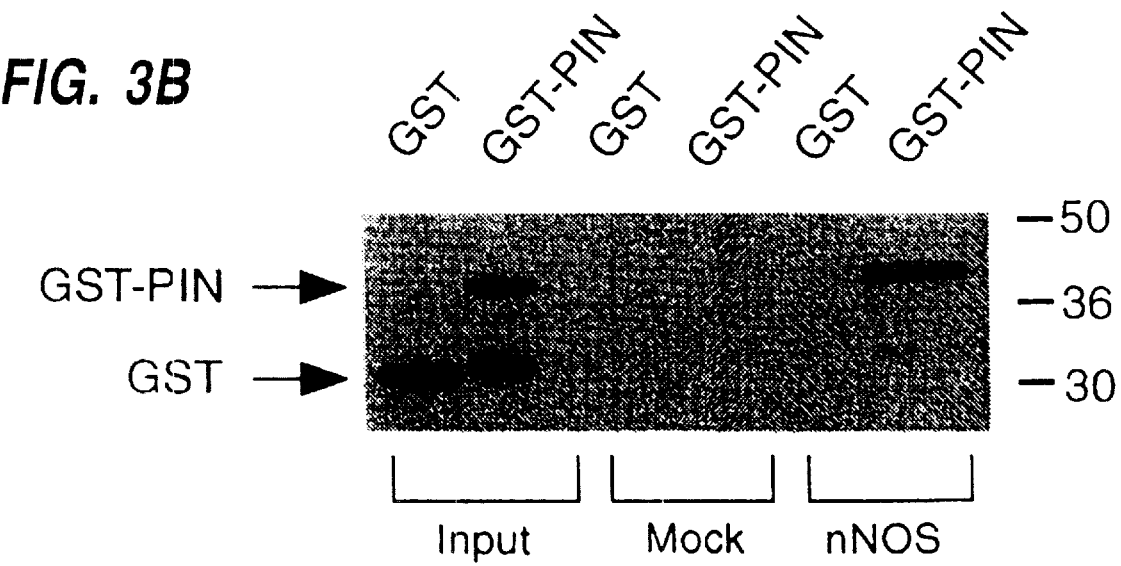
(FIG. 3B) GST-PIN-1 binds to nNOS immobilized on 2', 5', ADP-sepharose, a NOS affinity resin. Bacterial lysates containing the indicated recombinant proteins were mixed with lysates from nNOS transfected HEK 293 cells or mock transfected cells. The mixture was applied to 2', 5', ADP-sepharose and incubated for one hour at 4° C.; see Example 5, infra. The resin was washed extensively and the bound protein was eluted with 10 mM NADPH and detected by immunoblotting with an anti-GST antibody (NovaCastra). Aliquots of the bacterial lysates are included to show the mobilities of the different recombinant proteins.

We next employed a NOS affinity resin consisting of 2', 5' ADP-sepharose. Lysates from nNOS transfected HEK 293 cells were mixed with bacterial lysates containing either GST-PIN-1 or GST and applied to the 2', 5' ADP ribose resin, as described in Bredt et al., supra. GST-PIN-1 bound to the resin in the presence of nNOS, while GST failed to adhere to the resin (FIG. 3B).

Figure 3C:
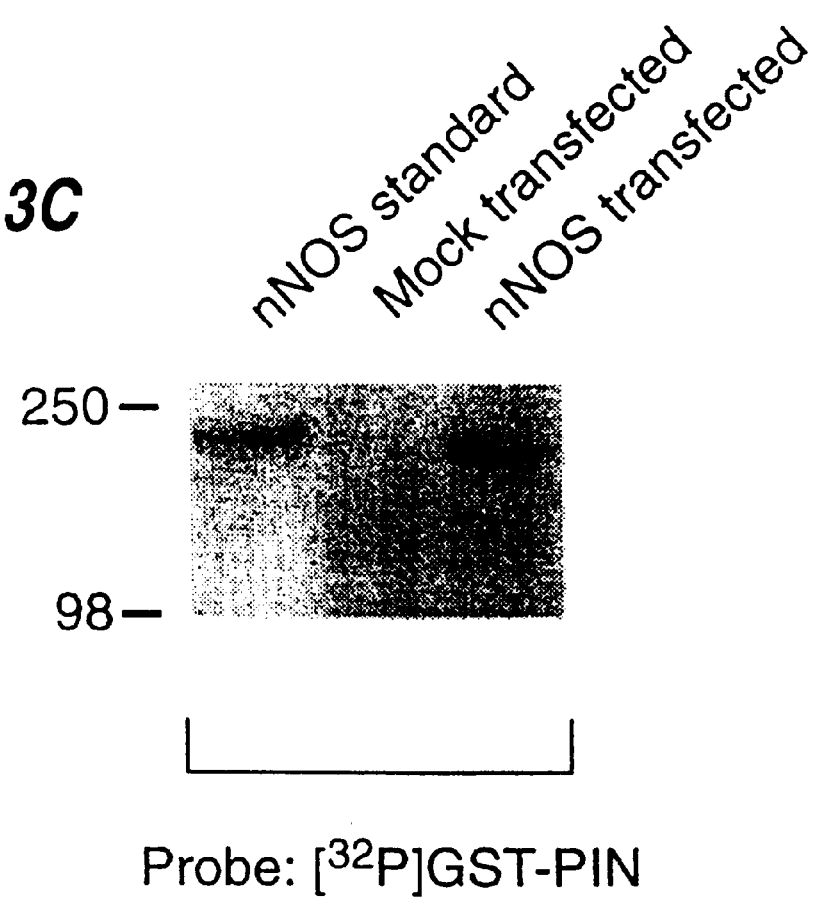
(FIG. 3C) GST-PIN-1 recognizes nNOS in a blot overlay assay. Two cyclic AMP-dependent protein kinase (PKA) sites were inserted between the GST moiety and PIN-1 to create a GST-PIN-1 fusion protein which was labelled in vitro with [g-$^{32}$P] ATP by PKA. Lysates were resolved by SDS-PAGE, transferred to nitrocellulose, and probed with the radiolabelled GST-fusion protein, as described in Example 5, infra. The radiolabelled protein binds to purified nNOS and to nNOS in transfected HEK 293 cells but not in mock transfected cells.

In a blot overlay assay, radiolabeled GST-PIN-1 selectively recognized nNOS in lysates from HEK 293 cells transfected with a plasmid expressing nNOS but not in mock transfected cells (FIG. 3C).

Figure 3D:
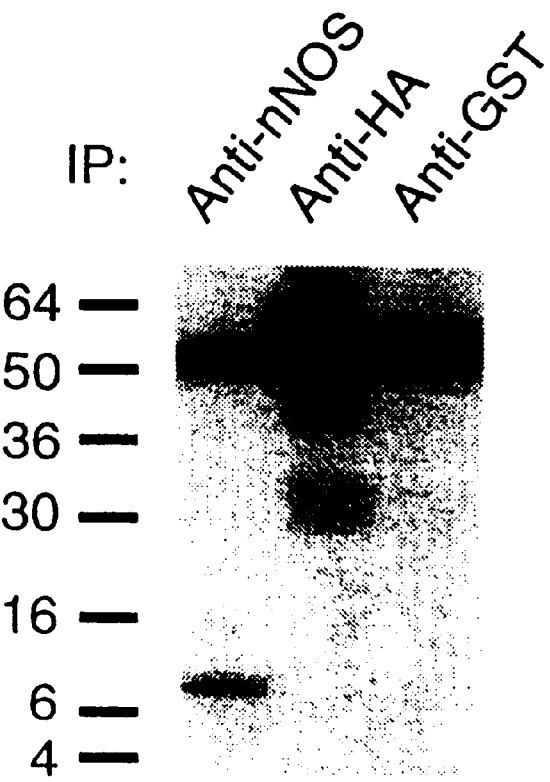
(FIG. 3D) nNOS coprecipitates with PIN-1. HEK 293 cells were transfected with nNOS and either a myc epitope-tagged PIN-1 construct or the parent vector. Preparation of this construct is described in Example 5, infra. Cell lysates were treated with an anti-myc antibody and the immunoprecipitates were immunoblotted with an anti-nNOS antibody to detect coprecipitation of nNOS.

To assess whether PIN-1 and nNOS stably interact in intact cells, we transfected nNOS into HEK 293 cells and cotransfected either PIN-1 tagged with the myc epitope or the parent vector. To construct the myc epitope-tagged PIN-1, a Sal I-Bgl II fragment comprising the entire translated sequence of the insert in pAD-PIN-1 was generated by PCR and subcloned into the Sal I-Bam HI site of the cytomegalovirus-driven eukaryotic expression vector pCMV-myc (a generous gift of A. Lanahan and P. Worley) to generate a fusion protein consisting of an N-terminal myc tag followed by a pentaglycine linker and the PIN-1 insert. The amino acid sequence preceding the PIN-1 insert in this fusion protein is as follows: MDQKLISEEDLNGGGGGST (SEQ ID NO: 16). HEK 293 cells were transfected with the indicated quantities of plasmids and cGMP levels were measured following treatment with 10 mM calcium ionophore A23187 for one hour. Cells were scraped and resuspended in 500 ml lysis buffer (20) and cGMP levels were measured by radioimmunoassay (Amersham). An anti-myc antibody immunoprecipitated NNOS only from cells transfected with myc-PIN-1 but not in mock transfected cells (FIG. 3D). Together these data show that NOS and PIN-1 physically interact.

EXAMPLE 6

This example demonstrates the physiological role of PIN-1.

To ascertain the physiological role of PIN-1, we cotransfected PIN-1 and nNOS in HEK293 cells and in NlE-115 mouse neuroblastoma cells. To determine whether PIN-1 might be an adapter protein targeting nNOS to a particular subcellular compartment, we conducted subcellular fractionation. In both of these cell lines nNOS distribution in soluble and various particulate fractions was identical in cells transfected with PIN-1 and in mock transfected cells.

Figure 4A:
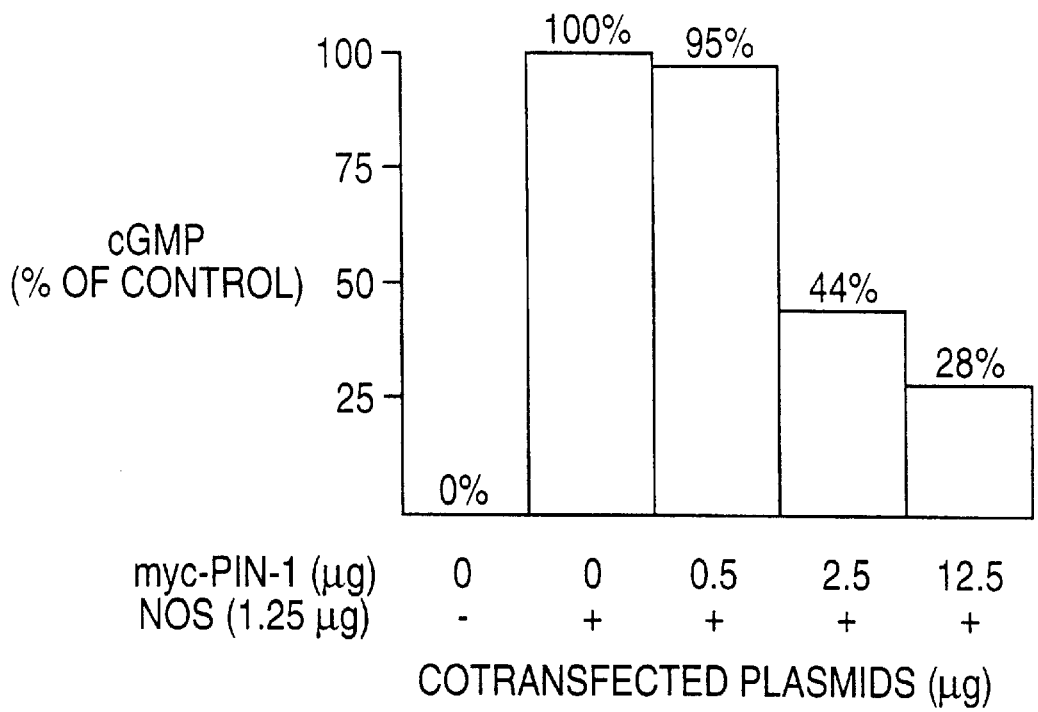
(FIG. 4A) PIN-1 reduces NO-dependent cGMP elevation in transfected HEK 293 cells. HEK 293 cells were transfected with an nNOS expression vector and the indicated concentrations of pmyc-PIN-1. Cells were treated with 10 mM calcium ionophore A23187 and cGMP levels were measured by radioimmunoassay.

We next assessed the influence of PIN-1 upon NO-dependent cGMP formation in HEK 293 cells cotransfected with PIN-1 and nNOS, as described in Example 5. Cotransfection of different amounts of PIN-1 together with nNOS produced a concentration-dependent reduction in calcium ionophore-stimulated cGMP formation (FIG. 4A). Transfection of PIN-1 alone did not alter basal cGMP levels or levels produced following stimulation with calcium iono-phore (J. E. Brenman et al., Cell 82, 743, 1995; J. E. Brenman et al., Cell 84, 757, 1996).

Figure 4B:
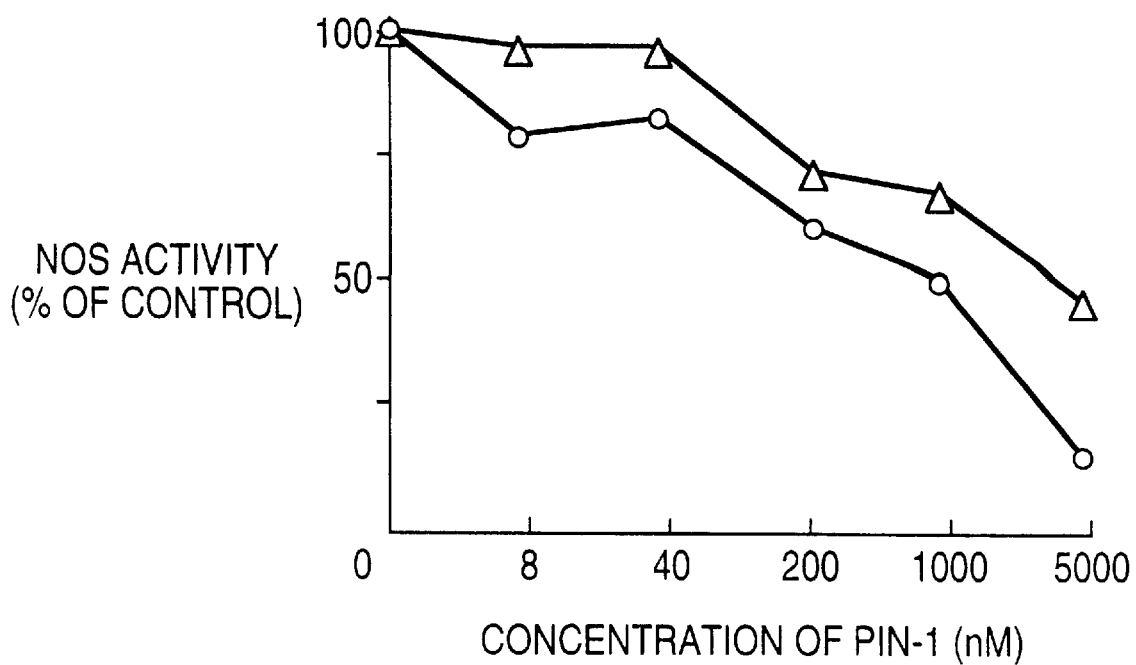
(FIG. 4B) PIN-1 inhibits nNOS catalytic activity in a concentration-dependent manner. GST-PIN-1 (●—●) and thrombin-cleaved PIN-1 (▲—▲) were expressed in *E. coli* and and incubated for one hour at 37° C. with transfected cell lysates containing nNOS. nNOS activity was measured by the measuring the accumulation of [$^3$H]citrulline from [$^3$H]arginine (28). Control activity levels were determined using either GST or thrombin cleaved BIRK, as described in Example 6, infra.

To determine whether PIN-1 directly inhibits nNOS, we examined the effect of purified recombinant GST-PIN-1 on nNOS activity in lysates of HEK 293 cells stably transfected with nNOS (FIG. 4B). As little as 250 nM PIN-1 substantially reduced NOS activity relative to the GST control with 50% inhibition evident at about 1 µM. Similar quantities of GST had no significant effect on NOS activity. We tested a second preparation of PIN-1 that utilized enzymatic cleavage of the GST moeity by thrombin. This preparation showed a similar dose-dependent inhibition of NOS activity, with 50% inhibition at about 5 mM (FIG. 4B). 22 Fusion proteins were prepared as described in Example 5, supra, except proteins were eluted from glutathione agarose by cleavage with thrombin in thrombin cleavage buffer (50 mM tris-HCl, pH 7.7, 100 mM NaCl, 2.5 mM CaCl2, and 1% Triton X-100) for 16 hours at 37° C. The eluate was adjusted to 5 mM EGTA, 4 mM leupeptin, and 400 nM aprotinin. Dilutions were made with thrombin cleavage buffer adjusted in this manner. A GST-BIRK fusion consisting of amino acids 347–442 of BIRK2 (D. S. Bredt et al., Proc. Natl. Acad. Sci. U.S.A. 92, 6753, 1995) was cleaved with thrombin as above and used as a control protein in NOS assays (a gift of N. A. Cohen). This reduction in affinity may be due to thermal denaturation during preparation.

Are the measured potencies compatible with a physiological role for PIN-1? A number of protein-protein interactions, such as those with with SH3 domains, have dissociation constants greater than 5 mM (H. Yu et al., Cell 76, 933, 1994; A. R. Viguera et al., Biochemistry 33, 10925, 1994). The abundance of the PIN-1 transcript by Northern blot suggests that PIN-1 is present at concentrations sufficient to inhibit nNOS activity in vivo.

EXAMPLE 7

This example demonstrates the mechanism of inhibition of neuronal nitric oxide synthase activity by PIN-1.

Figure 5A:
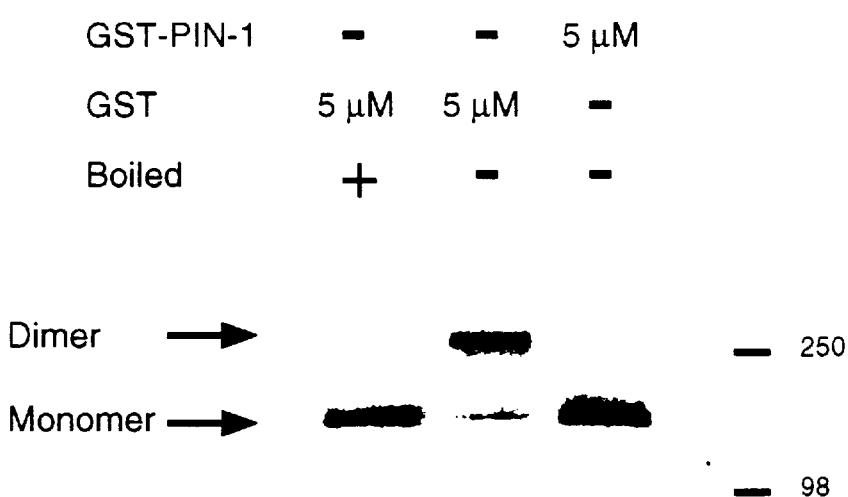
(FIG. 5A) nNOS migrates as a monomer after treatment with recombinant PIN-1. The nNOS dimer is stable in SDS-PAGE sample buffer but denatures and migrates at the expected monomeric molecular mass of 160 kD if the sample is boiled prior to electrophoresis (P. Klatt et al., *EMBO J.* 14, 3687, 1995). nNOS preparations from transfected HEK 293 cells similar to those in FIG. 4B were assayed for dimerization by SDS-PAGE. A boiled sample is included to show the expected mobility of the nNOS monomer.

We attempted to determine the mechanism of inhibition of nNOS activity by PIN-1. We considered the possibility that PIN-1 affects nNOS dimerization, which is thought to be essential for NOS activity (J. M. Hevel et al., J. Biol. Chem. 266, 289, 1991; H. H. H. W. Schmidt et al., Proc. Natl. Acad. Sci. U.S.A. 88, 365, 1991; D. J. Stuehr et al., Proc. Natl. Acad. Sci. U.S.A. 88, 7773, 1991; P. Klatt et al., EMBO 14, 3687, 1995). The subunits of nNOS form a dimer in the presence of tetrahydrobiopterin ($BH_4$) and arginine, which remains intact during low-temperature SDS-PAGE (Hevel et al., ibid.; Schmidt et al., ibid.; Stuehr et al., ibid.). In this assay, nNOS migrated as a monomer after being incubated with concentrations of GST-PIN-1 which inhibit >90% of NOS activity (FIG. 5A). Incubation with GST resulted in minimal loss of dimerized NOS.

Figure 5B:
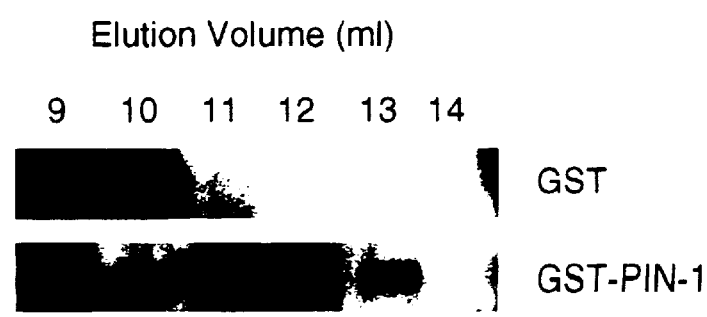
(FIG. 5B) The apparent molecular mass of nNOS by gel filtration is reduced following treatment with recombinant PIN-1. Samples were resolved by fast performance liquid chromatography using a Superdex 75 gel filtration column (Pharmacia). Fractions were concentrated and the material was immunoblotted with an anti-nNOS antibody. The void volume measured by blue dextran was 8.5 ml. The column was calibrated with the following standards: thyroglobulin ($M_r$ 670,000) 8.7 ml, gamma globulin ($M_r$ 158,000) 11.2 ml, ovalbumin ($M_r$ 44,000) 12.6 ml, myoglobin ($M_r$ 17,000) 14.3 ml, cyanocobalamin ($M_r$ 1,350) 19.0 ml.

We confirmed this effect by examining the apparent molecular mass of nNOS by gel filtration. The 320 kD NOS dimer has been shown previously by gel filtration to migrate with an apparent molecular mass of approximately 600 kD (P. Klatt et al., EMBO 14, 3687, 1995). NOS preparations that were incubated with GST migrated at approximately this apparent molecular mass (FIG. 5B). In the presence of GST-PIN-1, however, nNOS was detected at an elution volume consistent with NOS migrating as a monomer (FIG. 5B). These data suggest that PIN-1 promotes the dissociation of the nNOS dimer.

Dimerization of the three NOS isoforms is thought to be regulated by $BH_4$ and arginine binding. Thus, iNOS dimerizes in the presence of BH4 and arginine and monomerizes when these cofactors are removed by dialysis (Hevel et al., ibid.; Schmidt et al., ibid.; Stuehr et al., ibid.). The nNOS inhibitor 7-nitroindazole noncompetitively reduces the affinity of $BH_4$ and arginine (P. Klatt et al., *J. Biol. Chem.* 269, 13861, 1994) and causes NNOS to migrate as a monomer in SDS-PAGE (P. Klatt et al., *EMBO* 14, 3687, 1995). We have found that neither $BH_4$ nor arginine alter NOS binding to PIN-1 in vitro, implying that PIN-1 may alter dimerization through a mechanism distinct from 7-nitroindazole. Only one of two identified contributions to the stability of the nNOS dimer is sensitive to arginine and $BH_4$ sensisitive (Klatt et al., ibid.). In the SDS-PAGE stability assay, nNOS migrates as a monomer in preparations which include 7-nitroindazole or which lack $BH_4$ and arginine, but migrates as a dimer when assayed by gel filtration (P. Klatt et al., ibid). A second dimerization domain within nNOS may account for the 7-nitroindazole resistant dimerization. Using the yeast two-hybrid system we have recently found that the first 165 amino acids of nNOS, the PDZ domain, can dimerize. This region does not bind to BH4 or arginine but is adjacent to the PIN-1 binding site in NOS.

---

What is claimed is:

1. A method of screening test compounds for the ability to decrease or augment neuronal nitric oxide synthase (nNOS) activity, comprising the steps of:

(a) contacting a cell with a test compound, wherein the cell comprises:
        i) a first fusion protein comprising (1) a DNA binding domain and (2) a mammalian protein inhibitor of nNOS (PIN-1) protein as shown in SEQ ID NO:2;
        ii) a second fusion protein comprising (1) a transcriptional activating domain and (2) amino acids 163–245 of a nNOS protein as shown in SEQ ID NO:3 or a domain of a nNOS protein as shown in SEQ ID NO:4 which binds to the PIN-1 protein, wherein the interaction of the PIN-1 protein with amino acids 163–245 of the nNOS protein as shown in SEQ ID NO:3 or with the domain of the nNOS protein as shown in SEQ ID NO:4 reconstitutes a sequence-specific transcriptional activating factor; and
        iii) a reporter gene comprising a DNA sequence to which the DNA binding domain of the first fusion protein specifically binds; and (b) measuring the expression of the reporter gene; wherein a test compound that increases the expression of the reporter gene would be a potential drug for decreasing nNOS activity, and a test compound that decreases the expression of the reporter gene would be a potential drug for augmenting nNOS activity.

2. A method of screening for drugs with the ability to decrease or augment neuronal nitric oxide synthase (nNOS) activity comprising the steps of:

(a) contacting a cell with a test compound, wherein the cell comprises:

(i) a first expression vector comprising a subgenomic polynucleotide encoding nNOS as shown in SEQ ID NOS:3 or 4;
(ii) a second expression vector comprising a subgenomic polynucleotide encoding protein inhibitor of nNOS (PIN-1) as shown in SEQ ID NO:2; and
(b) measuring the amount of cGMP in the cell; wherein a test compound that increases the amount of cGMP would be a potential drug for augmenting nNOS activity, and a test compound that decreases the amount of cGMP would be a potential drug for decreasing nNOS activity.

3. The method of claim 1 wherein the second fusion protein comprises (1) transcriptional activating domain and (2) a nNOS protein as shown in SEQ ID NO:3.

4. The method of claim 1 wherein the second fusion protein comprises (1) transcriptional activating domain and (2) a nNOS protein as shown in SEQ ID NO:4.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 514 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Rattus norvegicus (xi) SEQUENCE DESCRIPTION: SEQ ID NO:1:

```
GGAGAGCGGC CGCGCTGTCG CCTCTGCTGT TTCAGCGGCG CCAGCACCTT CCCTAGGAGC      60

TCGCAGCAGC CGGCTGGCCC CTGCTCCACG GTAACCATGT GCGACCGGAA GGCGGTGATC     120

AAAAATGCAG ACATGTCGGA AGAGATGCAA CAGGACTCGG TGGAGTGCGC TACTCAGGCG     180

TTGGAGAAGT ACAACATAGA GAAGGATATC GCGGCCCATA TCAAGAAGGA GTTTGACAAG     240

AAGTACAACC CCACCTGGCA CTGCATCGTG GGCCGGAACT TCGGTAGCTA CGTGACACAC     300

GAGACCAAAC ACTTCATCTA CTTCTACCTG GGTCAGGTGG CCATTCTCCT GTTCAAATCT     360

GGTTAATAGC ATGGACTGTG CCAAACACCC AGTGATCCAT CCAAAAACAA GGACTGCATC     420

CTAAATTCCA AATACCAGAG ACTGAATCTT CAGCCTTGCT AAGGGAACAC CTCGTTTGAA     480

TCTGTTGTGT TTTGTACAGG GCACCGCCCA AGGA                                 514
```

(2) INFORMATION FOR SEQ ID NO:2:

(i) SEQUENCE CHARACTERISTICS:
      (A) LENGTH: 89 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Rattus norvegicus (xi) SEQUENCE DESCRIPTION: SEQ ID NO:2:

```
Met Cys Asp Arg Lys Ala Val Ile Lys Asn Ala Asp Met Ser Glu Glu
1               5                   10                  15

Met Gln Gln Asp Ser Val Glu Cys Ala Thr Gln Ala Leu Glu Lys Tyr
            20                  25                  30

Asn Ile Glu Lys Asp Ile Ala Ala His Ile Lys Lys Glu Phe Asp Lys
            35                  40                  45

Lys Tyr Asn Pro Thr Trp His Cys Ile Val Gly Arg Asn Phe Gly Ser
        50                  55                  60

Tyr Val Thr His Glu Thr Lys His Phe Ile Tyr Phe Tyr Leu Gly Gln
65                  70                  75                  80

Val Ala Ile Leu Leu Phe Lys Ser Gly
                85
```

(2) INFORMATION FOR SEQ ID NO:3:

(i) SEQUENCE CHARACTERISTICS:
        (A) LENGTH: 1554 amino acids
        (B) TYPE: amino acid
        (D) TOPOLOGY: linear (ii) MOLECULE TYPE: protein (vi) ORIGINAL SOURCE:
        (A) ORGANISM: Rattus norvegicus (xi) SEQUENCE DESCRIPTION: SEQ ID NO:3:

```
Met Glu Asp His Met Phe Gly Val Gln Gln Ile Gln Pro Asn Val Ile
1               5                   10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
            35                  40                  45

Gly Gly Ala Ala Glu Gln Ser Gly Leu Ile Gln Ala Gly Asp Ile Ile
        50                  55                  60

Leu Ala Val Asn Gly Arg Pro Leu Val Asp Leu Ser Tyr Asp Ser Ala
65                  70                  75                  80

Leu Glu Val Leu Arg Gly Ile Ala Ser Glu Thr His Val Val Leu Ile
            85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
            115                 120                 125

Pro Thr Lys Ala Val Asp Leu Ser His Gln Pro Pro Ala Gly Lys Glu
        130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
            165                 170                 175

Gly Leu Ala Pro Arg Pro Pro Gly Gln Asp Pro Ala Lys Lys Ala Thr
            180                 185                 190

Arg Val Ser Leu Gln Gly Arg Gly Glu Asn Asn Glu Leu Leu Lys Glu
            195                 200                 205

Ile Glu Pro Val Leu Ser Leu Leu Thr Ser Gly Ser Arg Gly Val Lys
        210                 215                 220

Gly Gly Ala Pro Ala Lys Ala Glu Met Lys Asp Met Gly Ile Gln Val
225                 230                 235                 240
```

-continued

```
Asp Arg Asp Leu Asp Gly Lys Ser His Lys Pro Leu Pro Leu Gly Val
            245                 250                 255
Glu Asn Asp Arg Val Phe Asn Asp Leu Trp Gly Lys Gly Asn Val Pro
            260                 265                 270
Val Val Leu Asn Asn Pro Tyr Ser Glu Lys Glu Gln Pro Pro Thr Ser
            275                 280                 285
Gly Lys Gln Ser Pro Thr Lys Asn Gly Ser Pro Ser Lys Cys Pro Arg
            290                 295                 300
Phe Leu Lys Val Lys Asn Trp Glu Thr Glu Val Val Leu Thr Asp Thr
305                 310                 315                 320
Leu His Leu Lys Ser Thr Leu Glu Thr Gly Cys Thr Glu Tyr Ile Cys
                325                 330                 335
Met Gly Ser Ile Met His Pro Ser Gln His Ala Arg Arg Pro Glu Asp
            340                 345                 350
Val Arg Thr Lys Gly Gln Leu Phe Pro Leu Ala Lys Glu Phe Ile Asp
            355                 360                 365
Gln Tyr Tyr Ser Ser Ile Lys Arg Phe Gly Ser Lys Ala His Met Glu
            370                 375                 380
Arg Leu Glu Glu Val Asn Lys Glu Ile Asp Thr Thr Ser Thr Tyr Gln
385                 390                 395                 400
Leu Lys Asp Thr Glu Leu Ile Tyr Gly Ala Lys His Ala Trp Arg Asn
                405                 410                 415
Ala Ser Arg Cys Val Gly Arg Ile Gln Trp Ser Lys Leu Gln Val Phe
            420                 425                 430
Asp Ala Arg Asp Cys Thr Thr Ala His Gly Met Phe Asn Tyr Ile Cys
            435                 440                 445
Asn His Val Lys Tyr Ala Thr Asn Lys Gly Asn Leu Arg Ser Ala Ile
            450                 455                 460
Thr Ile Phe Pro Gln Arg Thr Asp Gly Lys His Asp Phe Arg Val Trp
465                 470                 475                 480
Asn Ser Gln Leu Ile Arg Tyr Ala Gly Tyr Lys Gln Pro Asp Gly Ser
                485                 490                 495
Thr Leu Gly Asp Pro Ala Asn Val Gln Phe Thr Glu Ile Cys Ile Gln
            500                 505                 510
Gln Gly Trp Lys Pro Pro Arg Gly Arg Phe Asp Val Leu Pro Leu Leu
            515                 520                 525
Leu Gln Ala Asn Gly Asn Asp Pro Glu Leu Phe Gln Ile Pro Pro Glu
            530                 535                 540
Leu Val Leu Glu Val Pro Ile Arg His Pro Lys Phe Glu Trp Phe Lys
545                 550                 555                 560
Asp Leu Gly Leu Lys Trp Tyr Gly Leu Pro Ala Val Ser Asn Met Leu
                565                 570                 575
Leu Glu Ile Gly Gly Leu Glu Phe Ser Ala Cys Pro Phe Ser Gly Trp
            580                 585                 590
Tyr Met Gly Thr Glu Ile Gly Val Arg Asp Tyr Cys Asp Asn Ser Arg
            595                 600                 605
Tyr Asn Ile Leu Glu Glu Val Ala Lys Lys Met Asn Leu Asp Met Arg
            610                 615                 620
Lys Thr Ser Ser Leu Trp Lys Asp Gln Ala Leu Val Glu Ile Asn Ile
625                 630                 635                 640
Ala Val Leu Tyr Ser Phe Gln Ser Asp Lys Val Thr Ile Val Asp His
                645                 650                 655
His Ser Ala Thr Glu Ser Phe Ile Lys His Met Glu Asn Glu Tyr Arg
```

-continued

```
               660                  665                  670
Cys Arg Gly Cys Pro Ala Asp Trp Val Trp Ile Val Pro Pro Met
            675                  680                  685
Ser Gly Ser Ile Thr Pro Val Phe His Gln Glu Met Leu Asn Tyr Arg
    690                  695                  700
Leu Thr Pro Ser Phe Glu Tyr Gln Pro Asp Pro Trp Asn Thr His Val
705                  710                  715                  720
Trp Lys Gly Thr Asn Gly Thr Pro Thr Lys Arg Arg Ala Ile Gly Phe
                725                  730                  735
Lys Lys Leu Ala Glu Ala Val Lys Phe Ser Ala Lys Leu Met Gly Gln
                740                  745                  750
Ala Met Ala Lys Arg Val Lys Ala Thr Ile Leu Tyr Ala Thr Glu Thr
                755                  760                  765
Gly Lys Ser Gln Ala Tyr Ala Lys Thr Leu Cys Glu Ile Phe Lys His
        770                  775                  780
Ala Phe Asp Ala Lys Val Met Ser Met Glu Glu Tyr Asp Ile Val His
785                  790                  795                  800
Leu Glu His Glu Thr Leu Val Leu Val Val Thr Ser Thr Phe Gly Asn
                805                  810                  815
Gly Asp Pro Pro Glu Asn Gly Glu Lys Phe Gly Cys Ala Leu Met Glu
            820                  825                  830
Met Arg His Pro Asn Ser Val Gln Glu Glu Arg Lys Ser Tyr Lys Val
            835                  840                  845
Arg Phe Asn Ser Val Ser Ser Tyr Ser Asp Ser Gln Lys Ser Ser Gly
        850                  855                  860
Asp Gly Pro Asp Leu Arg Asp Asn Phe Glu Ser Ala Gly Pro Leu Ala
865                  870                  875                  880
Asn Val Arg Phe Ser Val Phe Gly Leu Gly Ser Arg Ala Tyr Pro His
                885                  890                  895
Phe Cys Ala Phe Gly His Ala Val Asp Thr Leu Leu Glu Glu Leu Gly
                900                  905                  910
Gly Glu Arg Ile Leu Lys Met Arg Glu Gly Asp Glu Leu Cys Gly Gln
            915                  920                  925
Glu Glu Ala Phe Arg Thr Trp Ala Lys Lys Val Phe Lys Ala Ala Cys
        930                  935                  940
Asp Val Phe Cys Val Gly Asp Asp Val Asn Ile Glu Lys Ala Asn Asn
945                  950                  955                  960
Ser Leu Ile Ser Asn Asp Arg Ser Trp Lys Arg Asn Lys Phe Arg Leu
                965                  970                  975
Thr Phe Val Ala Glu Ala Pro Glu Leu Thr Gln Gly Leu Ser Asn Val
            980                  985                  990
His Lys Lys Arg Val Ser Ala Ala Arg Leu Leu Ser Arg Gln Asn Leu
            995                  1000                 1005
Gln Ser Pro Lys Ser Ser Arg Ser Thr Ile Phe Val Arg Leu His Thr
    1010                 1015                 1020
Asn Gly Ser Gln Glu Leu Gln Tyr Gln Pro Gly Asp His Leu Gly Val
1025                 1030                 1035                 1040
Phe Pro Gly Asn His Glu Asp Leu Val Asn Ala Leu Ile Glu Arg Leu
                1045                 1050                 1055
Glu Asp Ala Pro Pro Val Asn Gln Met Val Lys Val Glu Leu Leu Glu
            1060                 1065                 1070
Glu Arg Asn Thr Ala Leu Gly Val Ile Ser Asn Trp Thr Asp Glu Leu
    1075                 1080                 1085
```

-continued

```
Arg Leu Pro Pro Cys Thr Ile Phe Gln Ala Phe Lys Tyr Tyr Leu Asp
        1090                1095                1100
Ile Thr Thr Pro Pro Thr Pro Leu Gln Leu Gln Gln Phe Ala Ser Leu
1105                1110                1115                1120
Ala Thr Ser Glu Lys Glu Lys Gln Arg Leu Leu Val Leu Ser Lys Gly
            1125                1130                1135
Leu Gln Glu Tyr Glu Glu Trp Lys Trp Gly Lys Asn Pro Thr Ile Val
                1140                1145                1150
Glu Val Leu Glu Glu Phe Pro Ser Ile Gln Met Pro Ala Thr Leu Leu
        1155                1160                1165
Leu Thr Gln Leu Ser Leu Leu Gln Pro Arg Tyr Tyr Ser Ile Ser Ser
    1170                1175                1180
Ser Pro Asp Met Tyr Pro Asp Glu Val His Leu Thr Val Ala Ile Val
1185                1190                1195                1200
Ser Tyr Arg Thr Arg Asp Gly Glu Gly Pro Ile His His Gly Val Cys
            1205                1210                1215
Ser Ser Trp Leu Asn Arg Ile Gln Ala Asp Glu Leu Val Pro Cys Phe
                1220                1225                1230
Val Arg Gly Ala Pro Ser Phe His Leu Pro Arg Asn Pro Gln Val Pro
        1235                1240                1245
Cys Ile Leu Val Gly Pro Gly Thr Gly Ile Ala Pro Phe Arg Ser Phe
    1250                1255                1260
Trp Gln Gln Arg Gln Phe Asp Ile Gln His Lys Gly Met Asn Pro Cys
1265                1270                1275                1280
Pro Met Val Leu Val Phe Gly Cys Arg Gln Ser Lys Ile Asp His Ile
            1285                1290                1295
Tyr Arg Glu Glu Thr Leu Gln Ala Lys Asn Lys Gly Val Phe Arg Glu
                1300                1305                1310
Leu Tyr Thr Ala Tyr Ser Arg Glu Pro Asp Lys Pro Lys Lys Tyr Val
        1315                1320                1325
Gln Asp Ile Leu Gln Glu Gln Leu Ala Glu Ser Val Tyr Arg Ala Leu
    1330                1335                1340
Lys Glu Gln Gly Gly His Ile Tyr Val Cys Gly Asp Val Thr Met Ala
1345                1350                1355                1360
Ala Asp Val Leu Lys Ala Ile Gln Arg Ile Met Thr Gln Gln Gly Lys
            1365                1370                1375
Leu Ser Ala Glu Asp Ala Gly Val Phe Ile Ser Arg Met Arg Asp Asp
                1380                1385                1390
Asn Arg Tyr His Glu Asp Ile Phe Gly Val Thr Leu Arg Thr Tyr Glu
        1395                1400                1405
Val Thr Asn Arg Leu Arg Ser Glu Ser Ile Ala Phe Ile Glu Glu Ser
    1410                1415                1420
Lys Lys Asp Thr Asp Glu Gly Phe Gln Leu Leu Thr Gly Pro Ser Cys
1425                1430                1435                1440
Pro Ala Gly Cys Lys Phe Cys Lys Arg Gly Gln Thr Leu Leu Asn Leu
            1445                1450                1455
Ser Ser Gly Thr Pro Cys Gly Pro Arg Ser Ala Ser Cys Pro Cys Arg
                1460                1465                1470
Cys Ala Leu Val Ser Leu Leu Gly Leu Leu Ala Pro Gln Trp Phe Pro
        1475                1480                1485
Arg Pro Ser Trp Val Tyr Ser Leu Ser Phe Pro Ala Ala Met Gln Cys
    1490                1495                1500
```

-continued

```
Phe Ser Asn Leu Gln Trp Leu Leu Gln Asn Ser Val Pro Thr Pro Ser
1505                1510                1515                1520

Leu Ala Asp Lys Gly Asn Ser Arg Val His Glu Thr Thr Gly Thr Trp
            1525                1530                1535

Pro Ser Leu Trp Gly Phe Phe Ser Leu Gly Phe Pro Trp Lys Gly Cys
            1540                1545                1550

Arg Asn
```

(2) INFORMATION FOR SEQ ID NO:4:

(i) SEQUENCE CHARACTERISTICS:
        (A) LENGTH: 1430 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:4:

```
Met Glu Glu Asn Thr Phe Gly Val Gln Gln Ile Gln Pro Asn Val Ile
1               5                   10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
            35                  40                  45

Gly Gly Ala Ala Glu Gln Ser Gly Leu Ile Gln Ala Gly Asp Ile Ile
50                  55                  60

Leu Ala Val Asn Asp Arg Pro Leu Val Asp Leu Ser Tyr Asp Ser Ala
65                  70                  75                  80

Leu Glu Val Leu Arg Gly Ile Ala Ser Glu Thr His Val Val Leu Ile
            85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
            115                 120                 125

Pro Thr Lys Ala Val Asp Leu Ser His Gln Pro Ser Ala Ser Lys Asp
            130                 135                 140

Gln Ser Leu Ala Val Asp Arg Val Thr Gly Leu Gly Asn Gly Pro Gln
145                 150                 155                 160

His Ala Gln Gly His Gly Gln Gly Ala Gly Ser Val Ser Gln Ala Asn
            165                 170                 175

Gly Val Ala Ile Asp Pro Thr Met Lys Ser Thr Lys Ala Asn Leu Gln
            180                 185                 190

Asp Ile Gly Glu His Asp Glu Leu Leu Lys Glu Ile Glu Pro Val Leu
            195                 200                 205

Ser Ile Leu Asn Ser Gly Ser Lys Ala Thr Asn Arg Gly Gly Pro Ala
            210                 215                 220

Lys Ala Glu Met Lys Asp Thr Gly Ile Gln Val Asp Arg Asp Leu Asp
225                 230                 235                 240

Gly Lys Ser His Lys Ala Pro Pro Leu Gly Gly Asp Asn Asp Arg Val
            245                 250                 255

Phe Asn Asp Leu Trp Gly Lys Asp Asn Val Pro Val Ile Leu Asn Asn
            260                 265                 270
```

```
Pro Tyr Ser Glu Lys Glu Gln Ser Pro Thr Ser Gly Lys Gln Ser Pro
         275                 280                 285

Thr Lys Asn Gly Ser Pro Ser Arg Cys Pro Arg Phe Leu Lys Val Lys
         290                 295                 300

Asn Trp Glu Thr Asp Val Val Leu Thr Asp Thr Leu His Leu Lys Ser
305                 310                 315                 320

Thr Leu Glu Thr Gly Cys Thr Glu His Ile Cys Met Gly Ser Ile Met
                 325                 330                 335

Leu Pro Ser Gln His Thr Arg Lys Pro Glu Asp Val Arg Thr Lys Asp
             340                 345                 350

Gln Leu Phe Pro Leu Ala Lys Glu Phe Leu Asp Gln Tyr Tyr Ser Ser
         355                 360                 365

Ile Lys Arg Phe Gly Ser Lys Ala His Met Asp Arg Leu Glu Glu Val
         370                 375                 380

Asn Lys Glu Ile Glu Ser Thr Ser Thr Tyr Gln Leu Lys Asp Thr Glu
385                 390                 395                 400

Leu Ile Tyr Gly Ala Lys His Ala Trp Arg Asn Ala Ser Arg Cys Val
                 405                 410                 415

Gly Arg Ile Gln Trp Ser Lys Leu Gln Val Phe Asp Ala Arg Asp Cys
             420                 425                 430

Thr Thr Ala His Gly Met Phe Asn Tyr Ile Cys Asn His Val Lys Tyr
         435                 440                 445

Ala Thr Asn Lys Gly Asn Leu Arg Ser Ala Ile Thr Ile Phe Pro Gln
         450                 455                 460

Arg Thr Asp Gly Lys His Asp Phe Arg Val Trp Asn Ser Gln Leu Ile
465                 470                 475                 480

Arg Tyr Ala Gly Tyr Lys Gln Pro Asp Gly Ser Thr Leu Gly Asp Pro
                 485                 490                 495

Ala Asn Val Gln Phe Thr Glu Ile Cys Ile Gln Gln Gly Trp Lys Ala
             500                 505                 510

Pro Arg Gly Arg Phe Asp Val Leu Pro Leu Leu Leu Gln Ala Asn Gly
         515                 520                 525

Asn Asp Pro Glu Leu Phe Gln Ile Pro Pro Glu Leu Val Leu Glu Val
530                 535                 540

Pro Ile Arg His Pro Lys Phe Asp Trp Phe Lys Asp Leu Gly Leu Lys
545                 550                 555                 560

Trp Tyr Gly Leu Pro Ala Val Ser Asn Met Leu Leu Glu Ile Gly Gly
                 565                 570                 575

Leu Glu Phe Ser Ala Cys Pro Phe Ser Gly Trp Tyr Met Gly Thr Glu
             580                 585                 590

Ile Gly Val Arg Asp Tyr Cys Asp Asn Ser Arg Tyr Asn Ile Leu Glu
         595                 600                 605

Glu Val Ala Lys Lys Met Asp Leu Asp Met Arg Lys Thr Ser Ser Leu
         610                 615                 620

Trp Lys Asp Gln Ala Leu Val Glu Ile Asn Ile Ala Val Leu Tyr Ser
625                 630                 635                 640

Phe Gln Ser Asp Lys Val Thr Ile Val Asp His His Ser Ala Thr Glu
                 645                 650                 655

Ser Phe Ile Lys His Met Glu Asn Glu Tyr Arg Cys Arg Gly Gly Cys
             660                 665                 670

Pro Ala Asp Trp Val Trp Ile Val Pro Pro Met Ser Gly Ser Ile Thr
         675                 680                 685

Pro Val Phe His Gln Glu Met Leu Asn Tyr Arg Leu Thr Pro Ser Phe
```

-continued

```
        690             695             700
Glu Tyr Gln Pro Asp Pro Trp Asn Thr His Val Trp Lys Gly Thr Asn
705             710             715             720
Gly Thr Pro Thr Lys Arg Arg Ala Ile Gly Phe Lys Lys Leu Ala Glu
                725             730             735
Ala Val Lys Phe Ser Ala Lys Leu Met Gly Gln Ala Met Ala Lys Arg
                740             745             750
Val Lys Ala Thr Ile Leu Tyr Ala Thr Glu Thr Gly Lys Ser Gln Ala
                755             760             765
Tyr Ala Lys Thr Leu Cys Glu Ile Phe Lys His Ala Phe Asp Ala Lys
                770             775             780
Ala Met Ser Met Glu Glu Tyr Asp Ile Val His Leu Glu His Glu Ala
785             790             795             800
Leu Val Leu Val Val Thr Ser Thr Phe Gly Asn Gly Asp Pro Pro Glu
                805             810             815
Asn Gly Glu Lys Phe Gly Cys Ala Leu Met Glu Met Arg His Pro Asn
                820             825             830
Ser Val Gln Glu Glu Arg Lys Ser Tyr Lys Val Arg Phe Asn Ser Val
                835             840             845
Ser Ser Tyr Ser Asp Ser Arg Lys Ser Ser Gly Asp Gly Pro Asp Leu
                850             855             860
Arg Asp Asn Phe Glu Ser Thr Gly Pro Leu Ala Asn Val Arg Phe Ser
865             870             875             880
Val Phe Gly Leu Gly Ser Arg Ala Tyr Pro His Phe Cys Ala Phe Gly
                885             890             895
His Ala Val Asp Thr Leu Leu Glu Glu Leu Gly Gly Glu Arg Ile Leu
                900             905             910
Lys Met Arg Glu Gly Asp Glu Leu Cys Gly Gln Glu Glu Ala Phe Arg
                915             920             925
Thr Trp Ala Lys Lys Val Phe Lys Ala Ala Cys Asp Val Phe Cys Val
                930             935             940
Gly Asp Asp Val Asn Ile Glu Lys Pro Asn Asn Ser Leu Ile Ser Asn
945             950             955             960
Asp Arg Ser Trp Lys Arg Asn Lys Phe Arg Leu Thr Tyr Val Ala Glu
                965             970             975
Ala Pro Asp Leu Thr Gln Gly Leu Ser Asn Val His Lys Lys Arg Val
                980             985             990
Ser Ala Ala Arg Leu Leu Ser Arg Gln Asn Leu Gln Ser Pro Lys Phe
                995             1000            1005
Ser Arg Ser Thr Ile Phe Val Arg Leu His Thr Asn Gly Asn Gln Glu
                1010            1015            1020
Leu Gln Tyr Gln Pro Gly Asp His Leu Gly Val Phe Pro Gly Asn His
1025            1030            1035            1040
Glu Asp Leu Val Asn Ala Leu Ile Glu Arg Leu Glu Asp Ala Pro Pro
                1045            1050            1055
Ala Asn His Val Val Lys Val Glu Met Leu Glu Glu Arg Asn Thr Ala
                1060            1065            1070
Leu Gly Val Ile Ser Asn Trp Lys Asp Glu Ser Arg Leu Pro Pro Cys
                1075            1080            1085
Thr Ile Phe Gln Ala Phe Lys Tyr Tyr Leu Asp Ile Thr Thr Pro Pro
                1090            1095            1100
Thr Pro Leu Gln Leu Gln Gln Phe Ala Ser Leu Ala Thr Asn Glu Lys
1105            1110            1115            1120
```

```
Glu Lys Gln Arg Leu Leu Val Leu Ser Lys Gly Leu Gln Glu Tyr Glu
            1125                1130                1135

Glu Trp Lys Trp Gly Lys Asn Pro Thr Met Val Glu Val Leu Glu Glu
            1140                1145                1150

Phe Pro Ser Ile Gln Met Pro Ala Thr Leu Leu Leu Thr Gln Leu Ser
            1155                1160                1165

Leu Leu Gln Pro Arg Tyr Tyr Ser Ile Ser Ser Ser Pro Asp Met Tyr
            1170                1175                1180

Pro Asp Glu Val His Leu Thr Val Ala Ile Val Ser Tyr His Thr Arg
1185                1190                1195                1200

Asp Gly Glu Gly Pro Val His His Gly Val Cys Ser Ser Trp Leu Asn
            1205                1210                1215

Arg Ile Gln Ala Asp Asp Val Val Pro Cys Phe Val Arg Gly Ala Pro
            1220                1225                1230

Ser Phe His Leu Pro Arg Asn Pro Gln Val Pro Cys Ile Leu Val Gly
            1235                1240                1245

Pro Gly Thr Gly Ile Ala Pro Phe Arg Ser Phe Trp Gln Gln Arg Gln
            1250                1255                1260

Phe Asp Ile Gln His Lys Gly Met Asn Pro Cys Pro Met Val Leu Val
1265                1270                1275                1280

Phe Gly Cys Arg Gln Ser Lys Ile Asp His Ile Tyr Arg Glu Glu Thr
            1285                1290                1295

Leu Gln Ala Lys Asn Lys Gly Val Phe Arg Glu Leu Tyr Thr Ala Tyr
            1300                1305                1310

Ser Arg Glu Pro Asp Arg Pro Lys Lys Tyr Val Gln Asp Val Leu Gln
            1315                1320                1325

Glu Gln Leu Ala Glu Ser Val Tyr Arg Ala Leu Lys Glu Gln Gly Gly
            1330                1335                1340

His Ile Tyr Val Cys Gly Asp Val Thr Met Ala Ala Asp Val Leu Lys
1345                1350                1355                1360

Ala Ile Gln Arg Ile Met Thr Gln Gln Gly Lys Leu Ser Glu Glu Asp
            1365                1370                1375

Ala Gly Val Phe Ile Ser Arg Leu Arg Asp Asp Asn Arg Tyr His Glu
            1380                1385                1390

Asp Ile Phe Gly Val Thr Leu Arg Thr Tyr Glu Val Thr Asn Arg Leu
            1395                1400                1405

Arg Ser Glu Ser Ile Ala Phe Ile Glu Glu Ser Lys Lys Asp Ala Asp
            1410                1415                1420

Glu Val Phe Ser Ser Pro
1425                1430

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GACTAGTCGA CTGAAGAGAA CACGTTTGGG                                      30
```

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

```
TCTGCAGATC TCAGTGGGCC TTGGAGCCAA A                                31
```

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

```
GACTGGTCG ACTGACGAGT TCTACCCCGC C                                 31
```

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

```
GGACTGGAGC TCATCTTGTT GGTC                                        24
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

```
GGACTGGTCG ACTCCTCTGC AGAAGAAGGT C                                31
```

(2) INFORMATION FOR SEQ ID NO:10:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

GGACTGGAGC TCTTACCAGA AAGGACACCA                              30

(2) INFORMATION FOR SEQ ID NO:11:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

TAGTCGACTC TCTTCAAACG CAAAGTG                                 27

(2) INFORMATION FOR SEQ ID NO:12:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

TAGTCGACTC AAGGCCATGG GCAGGGA                                 27

(2) INFORMATION FOR SEQ ID NO:13:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

GCAGATCTTT TGTGCGATTT GCCATC                                  26

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AATTCGTCGT GCATCTGTTG AACTACGTCG AGCTTCAGTT GCG        43

(2) INFORMATION FOR SEQ ID NO:15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

TCGACGCAAC TGAAGCTCGA CGTAGTTCAA CAGATGCACG ACG        43

(2) INFORMATION FOR SEQ ID NO:16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Met Asp Gln Lys Leu Ile Ser Glu Glu Asp Leu Asn Gly Gly Gly Gly
1                5                    10                  15

Gly Ser Thr